United States Patent [19]

LeMay

[11] 4,002,913
[45] Jan. 11, 1977

[54] RADIOLOGY

[75] Inventor: Christopher Archibald Gordon LeMay, Osterley, England

[73] Assignee: Emi Limited, Hayes, England

[22] Filed: May 8, 1975

[21] Appl. No.: 575,581

[30] Foreign Application Priority Data

May 9, 1974 United Kingdom ............ 20479/74

[52] U.S. Cl. .......................................... 250/445 T
[51] Int. Cl.² ........................................... G01T 1/16
[58] Field of Search .......... 250/402, 416, 490, 491, 250/360, 362, 359, 445 T

[56] References Cited

UNITED STATES PATENTS

| | | | |
|---|---|---|---|
| 3,106,640 | 10/1963 | Oldendorf | 250/360 |
| 3,158,744 | 11/1964 | Bernstein | 250/360 |
| 3,432,657 | 3/1969 | Slavin | 250/359 |
| 3,700,895 | 10/1974 | Dicke | 250/505 |
| 3,778,614 | 12/1973 | Hounsfield | 250/362 |
| 3,866,047 | 2/1975 | Hounsfield | 250/360 |

*Primary Examiner*—Alfred E. Smith
*Assistant Examiner*—B. C. Anderson
*Attorney, Agent, or Firm*—Fleit & Jacobson

[57] ABSTRACT

Radiological apparatus is described which is capable of performing analogue superposition of respective signals indicative of the absorption suffered by penetrating radiation on traversing each of a plurality of co-planar, linear paths through a body, some of which paths intersect. The signals are altered by processing to render them suitable for additive superposition, and the superposition is achieved by means of at least one charge storage tube. The altered signals, or signals related thereto, are applied to the target (or targets) of the tube (or tubes) and are deposited on respective linear regions thereof, the orientation of a linear region relative to the target (or targets) corresponding to the orientation relative to the body of the path giving rise to the relevant signal.

1 Claim, 1 Drawing Figure

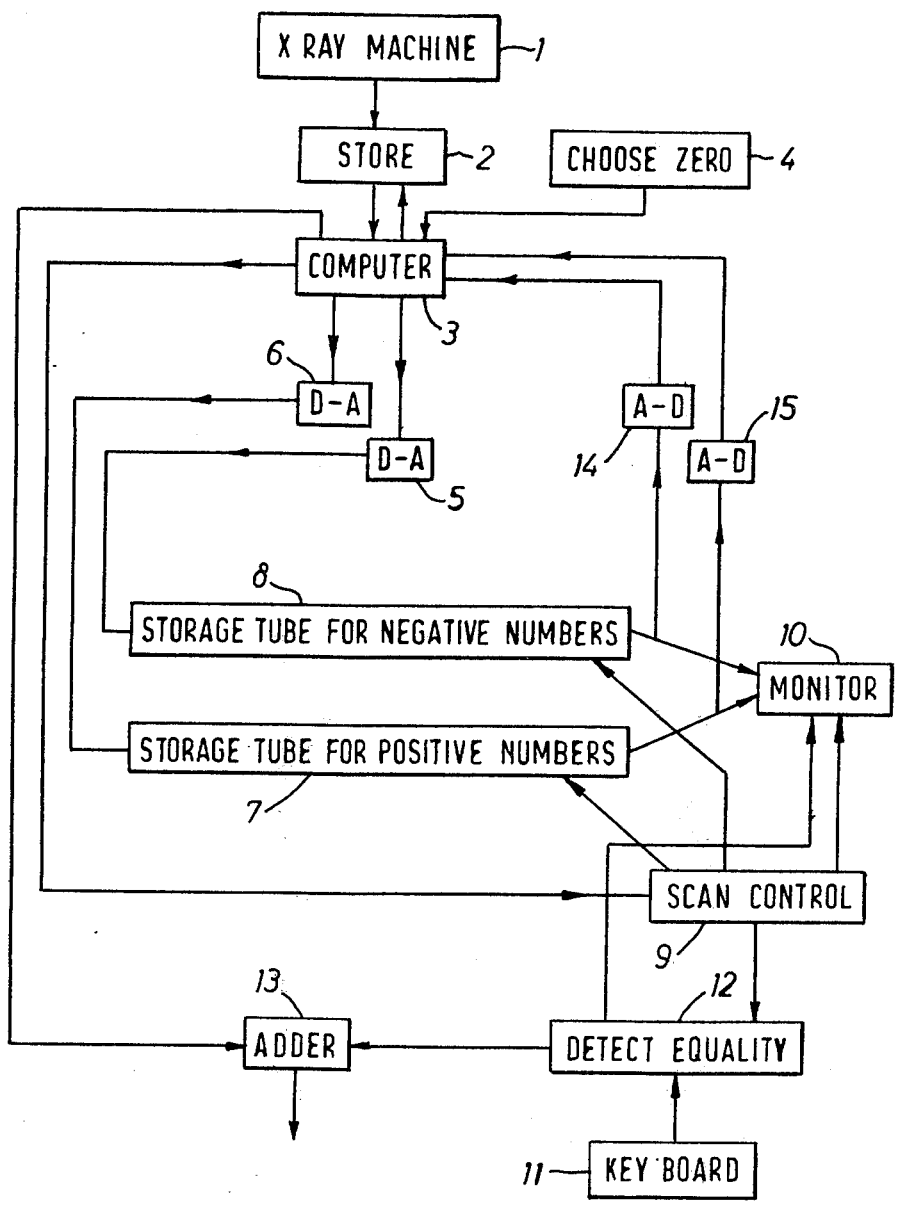

RADIOLOGY

The present invention relates to radiology.

Techniques are now known by means of which it is possible to obtain a highly accurate representation of the absorption or transmission coefficients of a two-dimensional array of elements notionally delineated in a cross-sectional plane through a body, or part of a body, being examined. One such technique is disclosed in U.S. Pat. No. 3,778,614.

In some circumstances it can be advantageous to have a visual representation of the aforementioned coefficients substantially as soon as the acquisition of the information used in forming the representation has been completed. Apparatus for providing such representations by means of a technique of analogue superposition is disclosed and claimed in U.S. Pat. No. 3,932,757. The present invention is an improvement in, or modification of, the apparatus disclosed and claimed in said U.S. Pat. No. 3,932,757.

According to the invention there is provided radiological apparatus including means for operating on respective electrical signals, indicative of absorption values for each of a plurality of co-planar paths transversed by penetrating radiation through a body, some of said paths being arranged to intersect, to produce respective altered signals which are susceptible to additive superposition, charge storage tube means having charge storage target means, input scanning means, associated with said storage tube means, for depositing upon said target means a respective line of charge indicative of each altered signal, the disposition of each such line of charge on said target means being indicative of the disposition, relative to the body, of the path to which the respective altered signal relates, output means for deriving from said target means output signals indicative of the accumulated charge deposited at different locations of said target means, and means for displaying said output signals.

In order that the invention may be clearly understood and readily carried into effect, it will not be described by way of example only with reference to the accompanying drawing, the single FIGURE of which shows a block diagrammatic form apparatus in accordance with one example of the invention.

Referring now to the drawing, an X-ray scanning machine, for example of the kind described in the aforementioned patent specification, is indicated at 1. This machine is arranged to direct radiation from a source through the body along many sets of co-planar linear paths towards detector means located on the other side of the body to the source. Each set of paths may comprise parallel or mutually divergent paths. The detector means is arranged to detect the radiation emergent from said body along each of said paths and thus provides so-called edge readings which represent the absorption suffered by the radiation on traversing each path through the body.

The edge readings, in digital form, are passed to a store 2, which can conveniently comprise a magnetic disc store, although any other kind of digital store could be used instead. The store 2 operates in co-operation with a digital computer 3, which can either be a general purpose computer or a special purpose computer, as it only has a limited set of duties to perform. The main purpose of the computer 3 is to alter the edge readings into a form which permits additive superposition in a manner to be described hereinafter, a suitable computation to effect the alteration of the edge readings being the convolution technique described and claimed in U.S. Pat. No. 3,924,129.

In most cases, patients to be examined by means of this apparatus will have already been subjected to a preliminary examination by a physician and thus a preliminary diagnosis will be available to indicate the form of malady from which the patient is suffering. In the light of such a preliminary diagnosis, the radiographer utilizing the apparatus is able to determine the particular substance within the body, such as fat, water or blood, which is most likely to reveal symptoms of the diagnosed malady, and he will wish to concentrate mainly upon this substance. The "zero" for the computation is selected in accordance with the absorption suffered by the X-radiation on traversing the substance of particular interest, and in practice it is best for this zero to be set a little above the black level on an output display monitor 10, as in this way various substances which exhibit absorptions close to that of the substance of particular interest are easily discernable on the monitor 10.

The "zero" referred to above is selected by means of a keyboard 4, and the selected level is used by the computer 3 as a threshold level for each of the altered edge readings. Thus the computer 3 is arranged to subtract the chosen zero level from each of the altered edge readings, and negative and positive results from the subtraction are applied respectively to digital-to-analogue converters 5 and 6. The converters 5 and 6 feed respective storage tubes 8 and 7 wherein each value is stored as a line of charge deposited under the control of respective input scanning circuits (not shown) upon the charge storage target of one or other of the tubes 7 and 8. The input scanning circuits are such that each line scanned thereby is orientated on a storage target in a corresponding manner to the orientation relative to the body of the path from which the respective edge reading was derived.

The position of the line is determined by a scan control unit 9 in response to timing signals from the computer 3. It will be realised that a sweep in a given direction executed by the X-ray machine later gives rise to a raster on the storage tubes in a corresponding direction, the raster being of parallel lines, like those of a normal television raster, which have been rotated to be parallel to the said direction.

In the simplest form of system, deposition of further information upon the targets of the storage tubes is inhibited once all of the altered edge readings have been deposited thereon. The derivation of the deposited information is then achieved by operating the storage tubes in a "read only" mode.

In an improved arrangement, the accuracy of the displayed image is increased by utilising the final values for each resolveable element of the storage tube targets and the initial edge readings to perform an iterative correction of the same general nature as that described in U.S. Pat. No. 3,778,614. Thus the final values of elements disposed along each beam path are read from the storage tubes and summed to give pseudo edge readings which are then compared with the corresponding true edge readings which, in this arrangement, have to be retained in the store. If there have been no errors in the digital-to-analogue conversion and re-conversion and if the storage tubes impart no errors to the data, then the result of the aforementioned comparison will be an error signal of zero. This will not, however, in general be the case and error signals will be fed back to the storage tubes to up-date the information stored therein, tending to cause the pseudo edge readings to approximate more closely to the true edge readings. The iterative procedure can continue for as long as an operator wishes to view the monitor 10, thus avoiding the possibility of errors arising due to decay of the informtion held in the storage tubes.

In the above mode of operation, the forward motion of the spots scanned over the storage tube targets along each line is used to read out information and the return motion along the same path is used for deposition of information. However, the forward motion of the spots can be used for both reading out and deposition of information if required.

It is not necessary to erase all the charge image on the target of a storage tube in the iteration process. If about half the stored charge is scanned off in order to obtain the video output, the correction signal can then be added to the residual charge pattern. The advantage of this approach lies in the absence of difficulties associated with storage tube picture "lag", which can slow down the iteration, and also greater ease of registration of the two scanning lines across the target.

If a scan line can be completed in 50$\mu$s and the spot can return along the same path in another 50$\mu$s scan frequency of 10000 Hz results, which is quite normal for television rasters. The total time to write in the picture, using the forward going lines only, is 160 × 3 × 180/10000 i.e. 8.64 seconds assuming 160 beams per set and 3 sets per degree of angular rotation around the body, for a total rotation angle of 180°. As this process can proceed during the X-ray exposure, very little time elapses after the end of the exposure before the image is complete.

As previously mentioned, the forward path along each scan line can be used as an output scan to pass the data to the monitor, subtractions being performed by an analogue circuit (not shown) as the input to the monitor.

If the operator chooses a new zero level on the keyboard 4, it takes 8.64 seconds for the apparatus to readjust completely to this new value. For this purpose the system must be switched back into the non-iterative mode using the convoluted data. As soon as the image is complete the system is again put into the iterative mode. In this way, readjustment starts at once and can be seen to be taking place.

The system is subject to the errors of analogue addition, which, although not great in this case, are probably greater than if a digital computer had performed the whole calculation. It is, however, a simple matter to add a facility which enables the value at a single point to be calculated accurately using only digital methods.

A second keyboard 11 provides analogue voltages in response to knob settings representing a position on the image. An equality detector 12 detects when the scan waveforms produce either the same $x$ value or the same $y$ value, where $x$ and $y$ are the cartesian co-ordinates of the desired point. When either occurs, a pulse is sent to the monitor. This results in the point on the image being marked by electronic "cross wires". When both $x$ and $y$ coincide with the required values, a signal is passed to the adder 13 which takes the digital signal which at that time is being provided by the computer and adds it on to the total. In this way, after 8.64 seconds in this example, an accurate value for the point is found. That is to say, when all contributions to the point have been added to it the sum will be the required value.

Using the same general principle within the computer 3, it is possible to calculate the absorption or transmission coefficients of the elements in any particular area more accurately than the capabilities of the storage tubes. Respective analogue to digital converters 14 and 15 can be used to compare the outputs of the storage tubes with the correct value at a particular point, and if they are found to be in error, corrections passed to the tubes via units 5 and 6 respectively. It will be appreciated that computer 3 contains a store in which these values of absorption (or transmission) coefficients for the elements of the matrix, as accurately computed in digital form are stored. The points used could either be chosen by a computer programme or be manually chosen from the keyboard 11. The connections for this last possibility have not been shown.

It is evident that the television type raster could be made a great deal faster if required. Data from the computer need only change once per line, i.e. once every 100$\mu$s. Even a general purpose digital computer could provide a considerably higher speed if this were required. The monitor could have a bandwidth of 25 mc/s, which means it could go 15 times faster than in the above example.

In an alternative arrangement, instead of using the return paths along the various lines as the output scan, a separate reading phase may be initiated after all the information has been applied to the targets, wherein the information is derived from the storage tubes 7 and 8 under the influence of output scanning circuits (not shown) which are arranged to scan simultaneously a fixed raster of television format on each of the storage targets. The monitor 10 is then set up to scan with the same waveforms as applied to the output scanning circuits of the storage tubes and the spot brightness is made to represent the difference between the outputs derived from the two storage tubes during the reading period. It will be appreciated, however, that in this case the persistence of the targets is taxed more heavily than in the arrangement previously described.

What we claim is:
1. A medical radiology diagnostic device for examining a body by penetrating X-radiation including: means for deriving, from a planar region of the body, electrical signals indicative of the absorption suffered by penetrating X-radiation traversing a plurality of sets of linear paths disposed at different positions in the plane of said planar region of the body, means for transforming said electrical signals in accordance with a convolution function to derive corresponding transformed signals, a storage tube having a target surface, means for storing on the target surface of the storage tube lines of charge each determined by the transformed electrical signal for a corresponding linear path of the X-radiation through the body and oriented on the target surface at an angle corresponding to the angle in said planar region of said corresponding linear path, a cathode ray tube having a display surface, and means for displaying on said display surface a visible brightness distribution corresponding to the charge distribution on the target surface of the storage tube.

* * * * *